United States Patent [19]
Augenlicht

[11] Patent Number: 5,569,584
[45] Date of Patent: Oct. 29, 1996

[54] METHOD FOR DISTINGUISHING OR MONITORING THE STATE OF PREMALIGNANT OR MALIGNANT TRANSFORMED HUMAN COLONIC TISSUE

[75] Inventor: Leonard H. Augenlicht, Redding, Conn.

[73] Assignee: Montefiore Medical Center, Bronx, N.Y.

[21] Appl. No.: 212,316

[22] Filed: Mar. 14, 1994

Related U.S. Application Data

[63] Continuation of Ser. No. 63,358, May 17, 1993, abandoned, which is a continuation of Ser. No. 805,102, Dec. 10, 1991, abandoned, which is a continuation of Ser. No. 182,185, Apr. 15, 1988, abandoned.

[51] Int. Cl.$^6$ .................................................. C12Q 1/68
[52] U.S. Cl. .................................. 435/6; 935/77; 935/78
[58] Field of Search .............................. 435/6; 935/77, 935/78

[56] References Cited

U.S. PATENT DOCUMENTS 4,981,783  1/1991  Augenlicht ................................. 435/6

FOREIGN PATENT DOCUMENTS

| 284362 | 3/1988 | European Pat. Off. . | |
|---|---|---|---|
| 8801031 | 8/1986 | WIPO | 435/6 |
| 8707305 | 12/1987 | WIPO | 536/27 |

OTHER PUBLICATIONS

Augenlicht et al., J. Biol. Chem. 259(3):1842–1847 (1984).

S. Anderson, et al. (1981) Sequence and organization of the human mitochondrial genome, *Macmillan Journals, Ltd*, 290:457–465.

L. H. Augenlicht, et al. (1987) Expression of cloned sequences in biopsies of human colonic tissue and in colonic corcinomer cells induces to differentiate in vitro, *Cancer Research*, 47: 6017–6021.

L. H. Augenlicht, et al. (1982) Cloning and screening of sequences expressed in a mouse colon tumor, *Cancer Research*, 42: 1088–1093.

Y. G. Capetanaki, et al. (1980) Comparison of polysomal and nuclear poly(A)–containing RNA populations from normal rat liver and Novikoff hepatoma, *Nucl. Acids Res.*, 8: 3193–3214.

M. Groudine, et al. (1980) Activation of cellular genes by avian RNA tumor viruses, Proc. *Natl. Acad. Sci. USA.*, 77: 5351–5354.

N. Hanania, et al. (1981) Manifold expression of new cellular genes in human lymphoid neoplasmia. *Proc. Natl. Acad. Sci. USA.*, 78: 6504–6508.

N. D. Hastie, et al. (1976) The expression of three abundance classes of messenger of RNA in mouse tissues. *Cell* 9: 761–774.

H. Jacobs, et al. (1980) Post–transcriptional regulation of messenger abundance in rat liver and hepatoma, 8: 3087–3103.

*Primary Examiner*—Stephanie W. Zitomer
*Attorney, Agent, or Firm*—Scully, Scott, Murphy & Presser

[57] ABSTRACT

The present application is directed to a method for distinguishing between normally differentiated and benign or malignantly transformed cells in human colonic tissue. It is also directed to a method for monitoring the state of premalignant or malignant human colonic tissue. In both methods, a 50F1 complementary DNA standard probe is utilized which hybridizes to the RNA in the test sample and to a second sample, which is a predetermined sample of colonic tissue, and the amount of hybridization of the 50F1 complementary DNA to the test sample is compared to the hybridization of the 50F1 complementary DNA with the second sample.

9 Claims, 7 Drawing Sheets

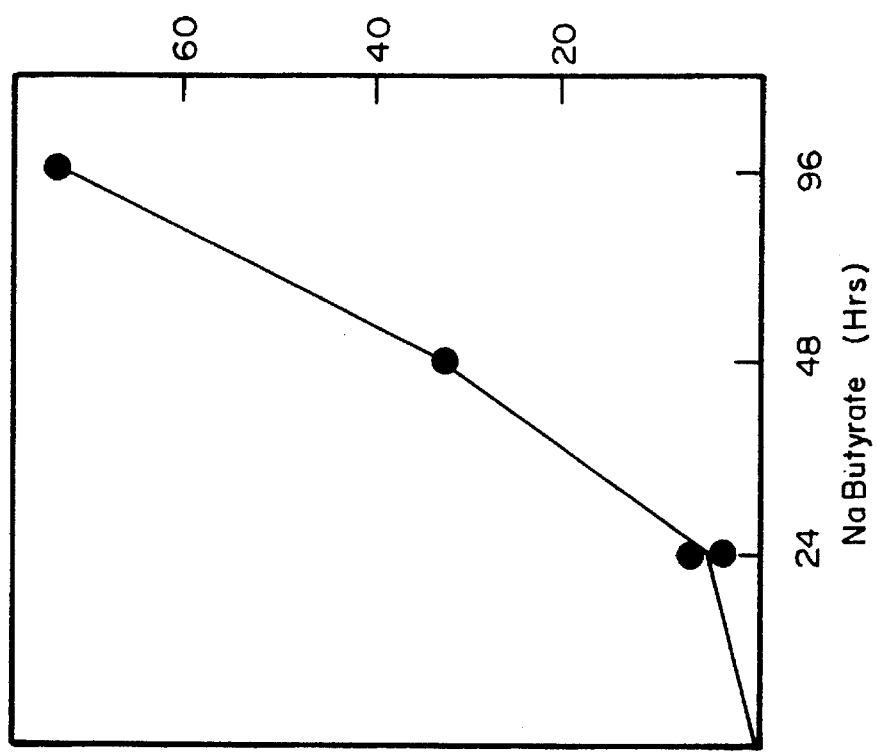
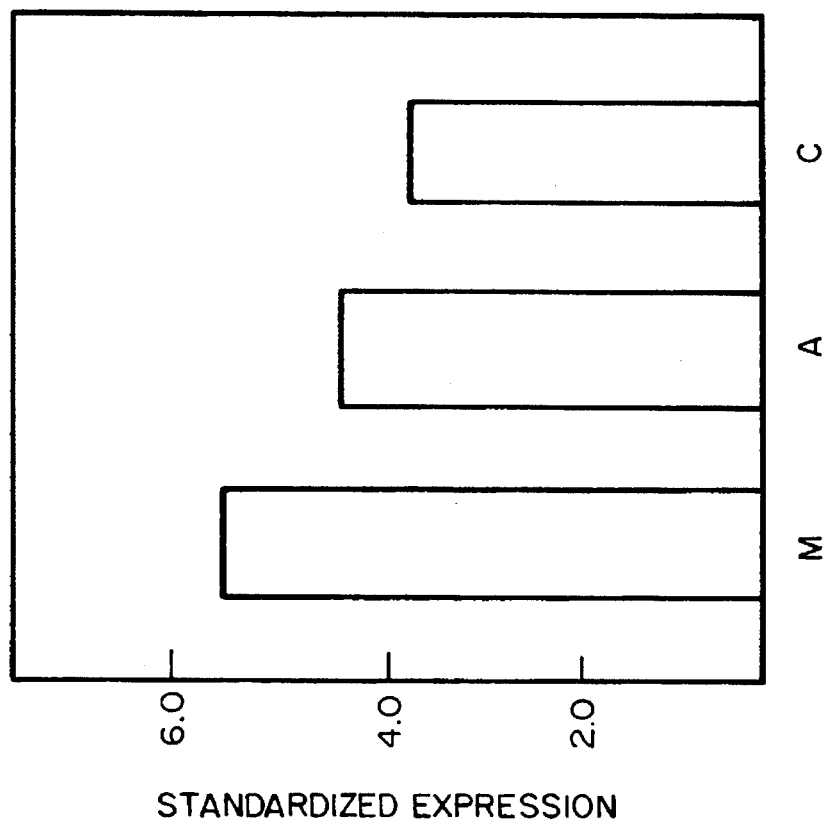
FIG.1B
FIG.1A

METHOD FOR DISTINGUISHING OR MONITORING THE STATE OF PREMALIGNANT OR MALIGNANT TRANSFORMED HUMAN COLONIC TISSUE

This invention was made with United States Government support under grant number 5RO1CA41372 awarded by the National Cancer Institute. The United States Government has certain rights in the invention.

This is a continuation of copending application(s) Ser. No. 063,358 filed on May 17, 1993 now abandoned, which is a continuation of Ser. No. 07/805,102 filed on Dec. 10, 1991, now abandoned, which is a continuation of Ser. No. 07/182,185, filed on Apr. 15, 1988, now abandoned.

FIELD OF THE INVENTION

The present invention relates to a method for determining the state of disease progression thereby providing a means for the detection of said disease and in the risk evaluation for the development of said disease. In particular, the present invention contemplates a method for determining and monitoring the state of malignant or premalignant progression or risk of development of malignant or premalignant progression in mammalian tissue and cells. Specifically, the present invention is directed to benign and malignant colon tumors and cells. The present invention is predicated on the discovery that the abundance of specific first nucleic acids changes in response to the disease state. The present invention is also directed to recombinant second nucleic acids useful in the detection and quantification of the first nucleic acids by hybridization. The present invention also contemplates the use of polypeptides encoded by said second nucleic acids in the regression and prophylaxis of disease states.

BACKGROUND OF THE INVENTION

Of the 50,000 to 100,000 genes present in the genome in higher vertebrates, approximately 10,000 are expressed in any tissue at a particular development stage. The level of expression (mRNA concentration or abundance) of each of these varies widely from 1 copy per cell (rare) to 50–300 (middle abundant) to 1,000 (highly abundant) (*Hastie and Bishop*, 1976, *Cell* 9: 761). The large number of biochemical, enzymatic and antigenic differences between normal cells and their transformed counterparts indicates that changes in level of expression of many of these genes (aside from mutations, deletions, amplifications or other structural alterations) is involved in development of the fully malignant cell. U.S. Pat. No. 4,981,783 teaches methods to analyze the expression of a large representation of these genes in order to characterize tissue or cells as normal, benignly or malignantly transformed, or at risk for transformation or other phenotypes (e.g., responsiveness to various drug or biological therapeutic agents; potential for metastasis and likely site) which are of clinical importance.

The initial work utilized a dimethylhydrazine induced mouse colon tumor as a model (*Augenlicht and Kobrin*, 1982, *Cancer Res.* 42: 1088). A cDNA library of the expressed genes of this tumor was constructed and 400 random selections made. Standard methodology was used to determine relative levels of expression of each of these 400 sequences in a number of normal and neoplastic tissues. A semi-quantitative scale was used, and analyses were repeated a number of times. Several general conclusions were drawn. First, approximately 15% of the sequences changed in expression in the colon tumor as compared to the normal mouse colonic mucosa. Most of these (12%) were modest quantitative shifts. This extent of change is similar to that documented in a number of other systems of transformation, including rat hepatomas (Capetanaki and Alonso, 1980, *Nuc. Acids Res.* 8: 3193; Jacobs and Birnie, 1980, *Nuc. Acids Res.* 8: 3087), human lymphoid neoplasia (Hanania, et al., 1981, *Proc. Natl. Acad. Sci.*, USA, 78: 6504), and most important, even the relatively well understood transformation of primary chick embryo fibroblasts by the Rous sarcoma virus (RSV) (Groudine and Weintraub, 1980, *Proc. Natl. Acad. Sci.*, USA, 77: 5351). Hence, even when the etiology of transformation is well understood (e.g., the introduction of the src gene by RSV and the expression of its product, pp60 sarc), the cell rapidly exhibits a large number of changes in gene expression which may include alterations in as many as 1000 sequences. Among those sequences whose normal expression was relatively restricted to the colon, there were many decreases (nineteen) in expression in colon tumors as well as modest increases (twenty three). Fewer changes (nine) were seen in the tumors among those sequences expressed in other normal tissues, but the alterations were of much larger magnitude (Augenlicht and Kobrin, supra).

In moving to the human, several significant changes were made. First, the number of sequences from a reference cDNA library made from the HT-29 human colon carcinoma cell line was increased to 4,000 (Augenlicht, et al., 1987, *Cancer Res.*, 47: 6017). This provided an 80% probability that every abundant and middle abundant sequence in this colon carcinoma cell line was represented in the data set. Second, methods were developed to accomplish the analysis of expression of each of these 4,000 sequences in very small human biopsies which yield 50–100 ng of poly A+ RNA. Utilizing a computerized scanning and image processing system, (Augenlicht, et al., supra; U.S. Pat. No. 4,981,783) relative level of expression of each of the 4000 sequences was quantitated in each biopsy. The number of sequences screened was reduced from 4000 in a series of experiments. First, all 4000 clones were evaluated in two biopsies of normal mucosa from individuals at low genetic risk for colon cancer; in two biopsies of benign adenoma from patients with the autosomal dominant disease familial polyposis; and in two biopsies of two different colon carcinomas. Sequences which were expressed at near background levels (low abundance) in all six of these biopsies, or which were modestly above background and showed no evidence of alteration in level of expression among the tissues, were eliminated. This left 379 clones for additional screening with other biopsies (Augenlicht, et al., supra).

Several facts emerged from the large data base generated. First, the overall number of sequences which changed in expression between human colon carcinomas and normal human colonic mucosa was approximately 7%, which is the same order of magnitude as the extent of change seen in other systems cited above. Furthermore, the change was progressive, in that fewer alterations were seen in benign tumors (adenomatous polyps) than in malignant carcinomas when both were compared to normal tissue—the flat mucosa from patients at low genetic risk for colon cancer. Finally, the flat mucosa from patients with familial polyposis who are at very high risk for development of colon cancer showed much greater changes in gene expression when compared to low-risk normal mucosa than either the benign polyps that arise in this disease or the carcinomas. Hence, the high-risk tissue, having undergone many constitutive alterations in association with the inherited gene defect, may be primed for progression along any of many pathways to malignancy.

This same methodology and reference library was then used to analyze changes in gene expression in HT-29 and SW-480 colon carcinoma cell lines induced to differentiate in vivo with sodium butyrate. Again, many alterations in gene expression were found, but a comparison of the in vivo and in vitro data bases allowed selection of eight sequences whose relative levels of expression characterized colonic cells as either differentiated or fully transformed. Further, the quantitative extent of change in these sequences in vivo and in vitro was similar, with a linear correlation coefficient which was significant for a comparison of the in vivo and in vitro data at the p<0.01 level. The in vivo data establish that the in vitro results are not tissue culture artifacts but do in fact bear a relationship to the human disease. Conversely, the in vitro data could be confirmed by standard Northern blot analysis, thus validating the scanning and image processing methodology, and also reduce the complexity of cell types and human tissue variability for further analysis of these sequences.

In accordance with the present invention, it has been discovered that expression of one of the aforementioned sequences can be used to determine the state of benign and malignant colon tumors as compared to the normal colonic mucosa, thus fulfilling an important need to monitor such tumors.

SUMMARY OF THE INVENTION

The present invention contemplates a method for determining the state of malignant or premalignant progression or risk for development of malignant or premalignant progression in mammalian tissues and cells which comprises identifying a statistically significant differential in detected abundance of an RNA isolated from the tissue to be studied relative to a predetermined standard, ie., abundance value obtained from tissue isolated from a particular population.

The present invention is also directed to a recombinant nucleic acid molecule useful in the detection of the aforementioned RNA.

Another aspect of the present invention relates to a polypeptide encoded by said recombinant nucleic acid molecule.

Still another aspect of the present invention contemplates a method for regression and inhibition of growth of malignant and benign colonic tumors by the administration of an effective amount of the aforementioned polypeptide with a pharmaceutically acceptable carrier.

BRIEF DESCRIPTION OF THE FIGURES

FIG. I(A) is a bar diagram depicting expression of 50F1 in biopsies taken from normal mucosa (M), adenomas (A) and colon carcinomas (C).

FIG. 1 (B) is a graphical representation of expression of 50F1 in tissue culture (in vitro) following treatment of HT29 colon carcinoma cells with sodium butyrate.

DETAILED DESCRIPTION OF THE INVENTION

The present invention contemplates a method for determining the state of malignant or premalignant progression or risk for development of malignant or premalignant progression in mammalian tissues and cells which comprises identifying a statistically significant differential in detected abundance of an RNA isolated from the tissue to be studied relative to a standard. The selection of said standard being determined by the analysis being conducted. For example, if cancer states are to be detected in a random population, the standard is a predetermined abundance obtained from a normal population (i.e., free from detectable cancer and genetically at low risk). If the analysis is to monitor the effectiveness of an anticancer treatment, said standard is a predetermined abundance obtained from an anormal (cancerous or benignly transformed) population. In one preferred embodiment, the mammalian tissue is human colonic mucosa but the skilled artisan will recognize the applicability of the method disclosed herein to a wide variety of tissue such as breast, pancreatic, stomach, lung, oral, cerebral, intestinal and the like.

More particularly, the present invention contemplates a method for determining the state of malignant or premalignant progression or risk for development of malignant progression in human colonic mucosa or colon cells which comprises determining the relative abundance of an RNA, said RNA being represented in a first nucleic acid isolated from the tissue to be studied and immobilized onto a solid support, by contacting to said first nucleic acid, a second nucleic acid in probe form, said second nucleic acid characterized by possessing a copy number variably represented in different normal human tissues, such that the second nucleic acid, or part thereof, will hybridize to said RNA, the hybridization quantified by exposing said second nucleic acid contacted with said RNA to a detecting means.

The present invention is predicated on the surprising discovery that a group of nucleic acid sequences, characterized herein as possessing copy numbers variably represented in different normal mammalian tissue compared to other nucleic acid sequences which are relatively constant in their representation in the same tissue. In accordance with the present invention, a simple dot-blot method is described enabling the rapid determination of the variable or constant copy number of a particular sequence.

Figure 2:
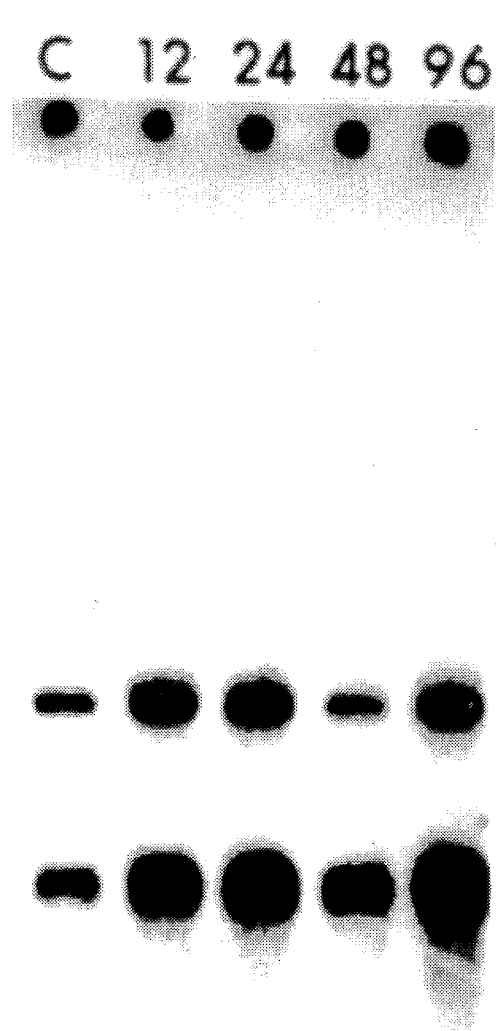
FIG. 2 is a photographic representation of a Northern blot analysis of RNA from HT29 cells from 12 hours to 96 hours exposed to sodium butyrate. "C" represents a control.
Figure 7:
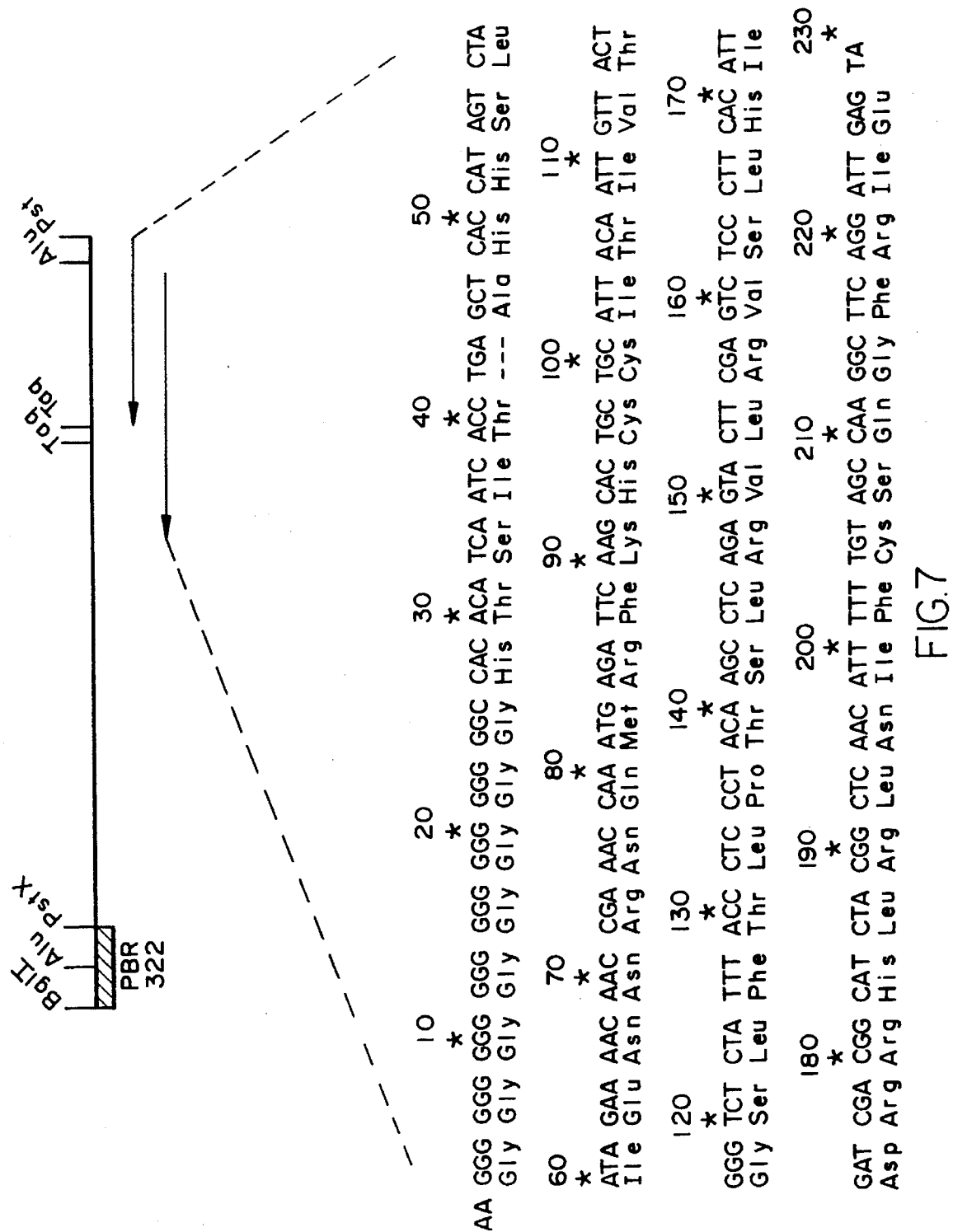
FIG. 7 is a diagrammatic representation of the cDNA clone 50F1 showing nucleotide sequence and partial restriction map.

In a specific embodiment, a nucleic acid sequence possessing a copy number which is variably represented is designated herein 50F1, isolated from human colonic mucosa and is further defined by its nucleotide sequence given in FIG. 7. In accordance with the present invention, expression of 50F1 progressively decreases in benign and malignant colon tumors in humans as compared to the normal colonic mucosa (FIG. 1A) and increases back to the level characteristic of normal mucosa when HT29 colon carcinoma cells in vitro are induced to differentiate by exposure to 5 mM sodium butyrate (FIG. 1B). Northern blot analysis of RNA from HT29 cells confirms this increase in expression at 24 to 96 hours following treatment with sodium butyrate (FIG. 2).

Figure 3:
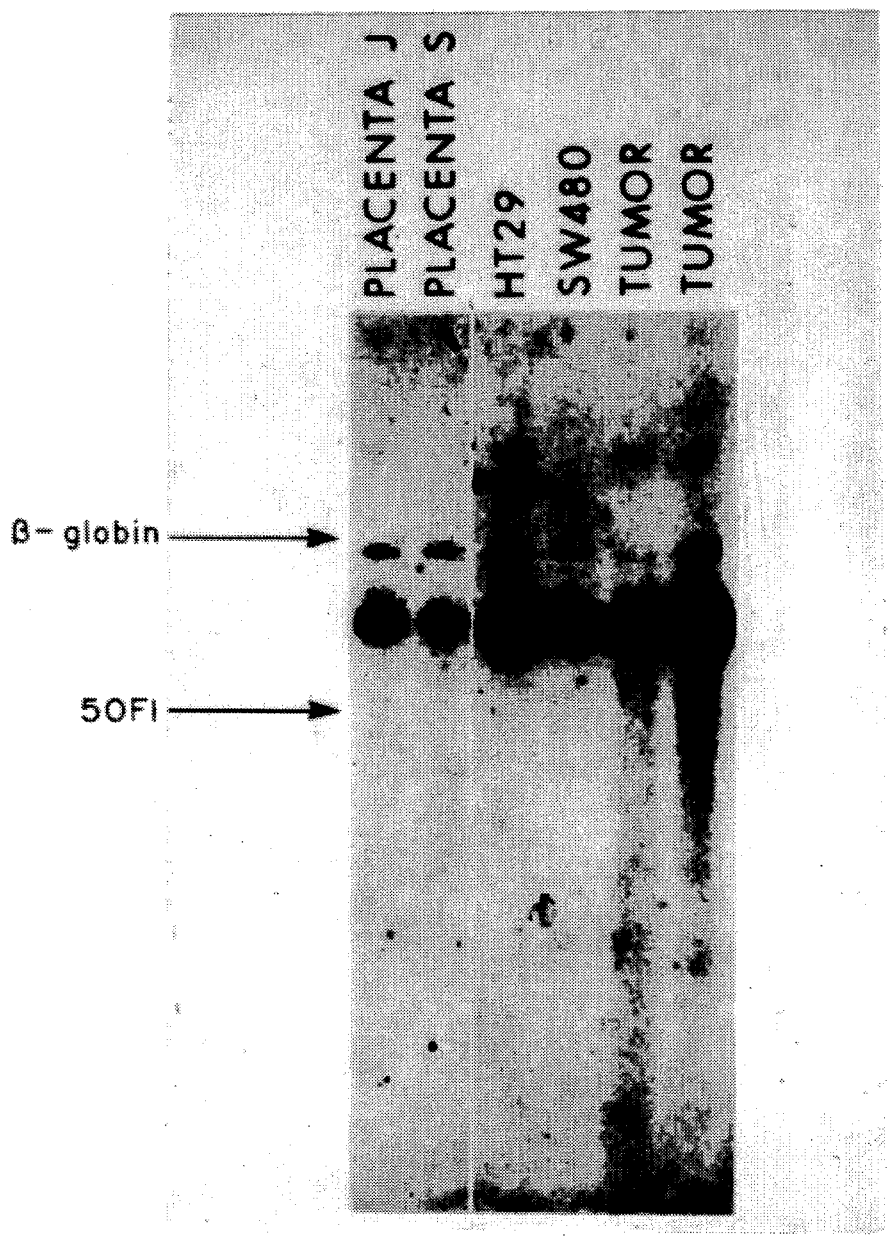
FIG. 3 is a photographic representation of a Southern blot analysis of genomic DNA from different tissues hybridized with 50F1.

Southern blot analysis demonstrates that the copy number of this sequence is elevated in the genomic DNA isolated from the colon carcinoma cell lines HT29 and SW480 and in genomic DNA from two colon tumors relative to the level in the DNA from two normal human placentas (FIG. 3).

Accordingly, one of the many benefits of the present invention is the discovery of a nucleic acid sequence useful in determining the state of malignant or premalignant progression or risk of development of malignant or premalignant progression. As previously indicated, many such nucleic acid sequences are contemplated which may be useful in the practice of this invention. The present invention is disclosed using one particular sequence (50F1) which, up to the present time, has been determined to be most useful in practicing this invention. This is done, however, with the understanding that the present invention encompasses all such sequences.

For example, in accordance with the subject invention, a series of experiments was carried out in which genomic DNA was isolated from a number of normal human tissues and hybridized to one of the aforementioned nucleic acid sequences, designated herein 50F1. Level of hybridization, and hence, relative copy number of the sequence, was determined by careful attention to quantitation and standardization of the hybridization results. This was done as follows. A measured amount of each DNA sample (approximately 1 micrograms) was applied to nitrocellulose in duplicate at 2 positions using a standard 96 position (8×12 format) dot-blot apparatus (Schleicher and Schuell, Inc.). The duplicate dots were not adjacent on the dot-blot. They were placed at sites distal to each other to avoid potential systematic error due to position effects during application, hybridization, washing, or film exposure. Similarly, several positions throughout the dot-blot were left blank for background correction. The source of the DNA samples varied (below), but every blot contained duplicate positions of DNA from placenta J which therefore provided a standard between experiments. Finally, every dot-blot was made in replicate so that one copy could be hybridized to the sequence of interest (e.g., 50F1) and a replicate to a standard (e.g., human β-globin). This was used to correct for potential differences in the amount of DNA loaded per dot for eachsample.

A $^{32}$P labeled probe was made using the insert of either 50F1 or human β-globin using the well known nick-translation procedure and each hybridized to a replicate of a dot-blot. Following washing, the blots were exposed to X-ray film to obtain a visual image of the relative hybridization of each probe to each DNA sample.

For quantitation, the following procedure was used. The dot-blot was cut into sections, each section being the location of one dot (i.e., one DNA sample). Each section was then placed into liquid scintillation fluid and the extent of hybridization of the probe to the DNA determined by recording the counts per minute for each section in a scintillation counter (Packard Tricarb).

Calculation was then done as follows. The mean hybridization for each DNA sample, done at least in duplicate on a blot was calculated. Similarly, the mean background was calculated from the blank spots. The mean background for a blot was then subtracted from the mean hybridization for each DNA sample on that blot. For each DNA sample, a corrected value was determined by calculating the ratio: mean hybridization 50F1/mean hybridization β-globin, the latter data being determined in the same way from the replica blot which had been hybridized to a human β-globin probe and having been standardized by reference to placenta J on that blot. Finally, standardization between experiments was established by taking this calculated 50F1 value for each DNA sample and expressing it as a ratio to the value calculated similarly for the DNA sample placenta J, which was included on every blot.

In summary, these calculations correct for differences in determination of amount of DNA applied to the dot-blot, and differences between experiments (e.g., probe specific activity, conditions of hybridization).

Experiments done and calculated in the manner described have yielded the following results. For purposes of description, differences in hybridization level between genomic DNA of different samples or tissues are referred to as differences in copy number of the sequence (i.e., 50F1) in the genome.

Figure 4:
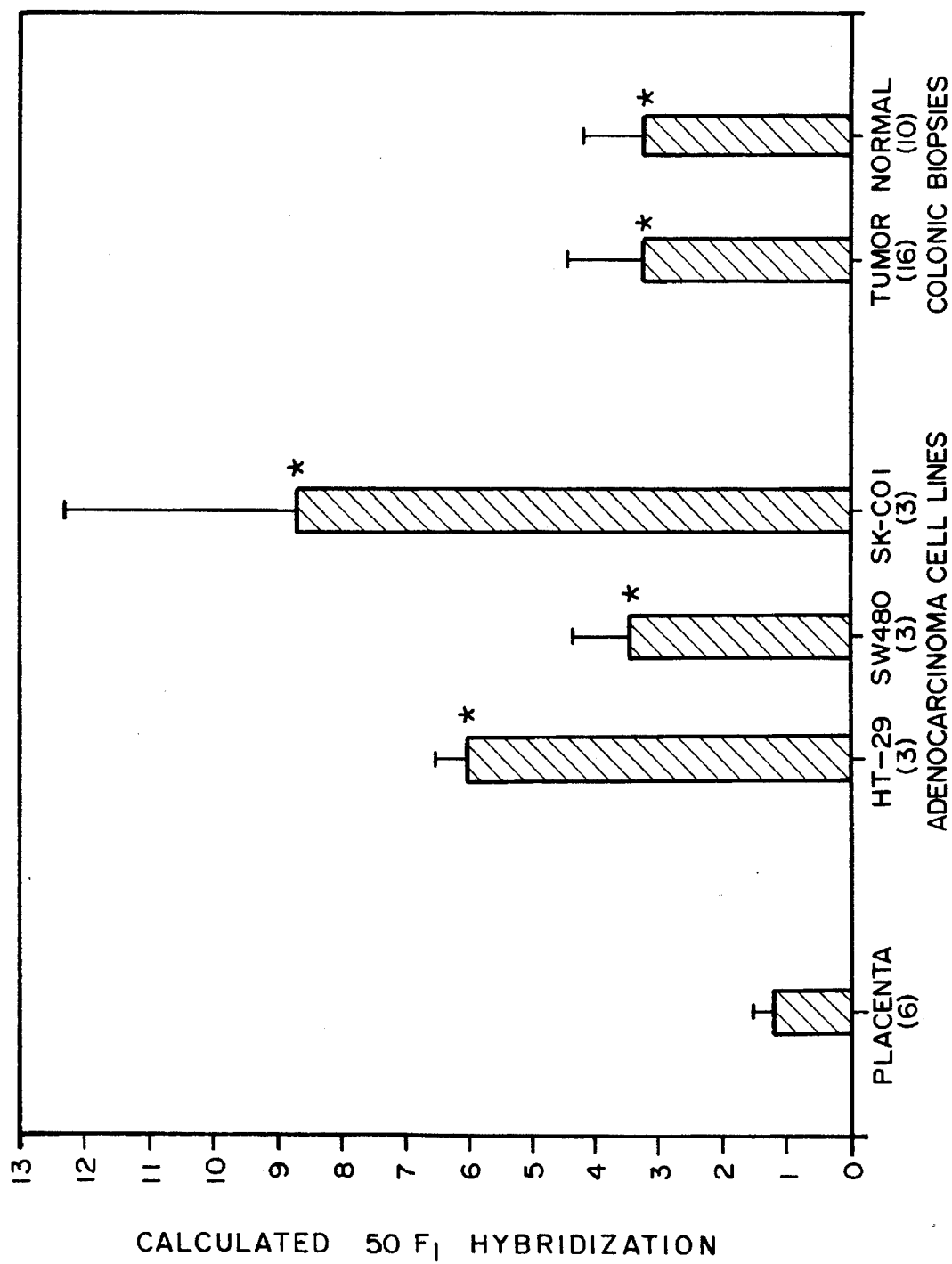
FIG. 4 is a bar diagram depicting copy number of 50F1 (the numbers in parentheses below the diagram indicate the number of samples tested) in different tissue samples.
Figure 5:
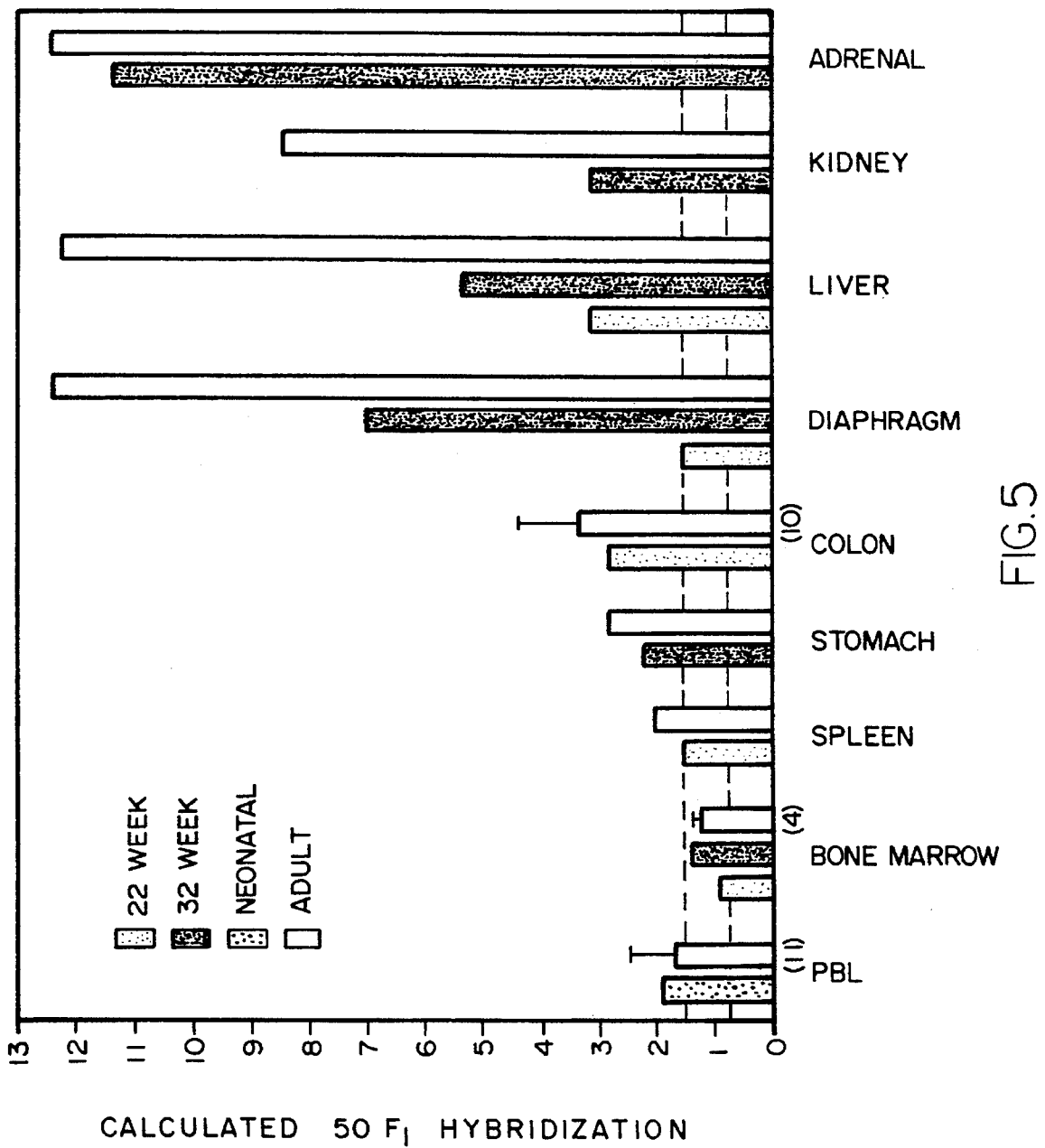
FIG. 5 is a bar diagram depicting copy number of 50F1 in different tissue samples at different stages of development (the numbers in parentheses below the diagram indicate the number of samples tested).

FIG. 4 illustrates that relative to the mean of 6 different placentas, the copy number of 50F1 is elevated three to nine fold in 3 colon carcinoma cell lines (HT29, SW480 and SKC01). A three fold elevation was also seen in genomic DNA from colon tumors and a similar elevation was seen in the normal human colonic mucosa. In FIG. 5, the range for the 6 placentas is shown as 2 horizontal lines (approximately 0.8–1.6). FIG. 5 illustrates that the copy number differs over a wide range among different tissues and at different developmental stages (gestational age of the fetus). No difference is detected among the placentas, peripheral blood leukocytes (PBL), bone marrow, and spleen at any developmental stage. Stomach shows a slight elevation at 32 weeks, somewhat higher in the adult. The three fold elevation in colon is essentially established by 22 weeks. No increase is seen in diaphragm at 22 weeks, but this rapidly increases to seven fold at 32 weeks and 12 fold in the adult. Liver, kidney, and adrenal similarly show progressive increases in 50F1 copy number with developmental stage.

Figure 6:
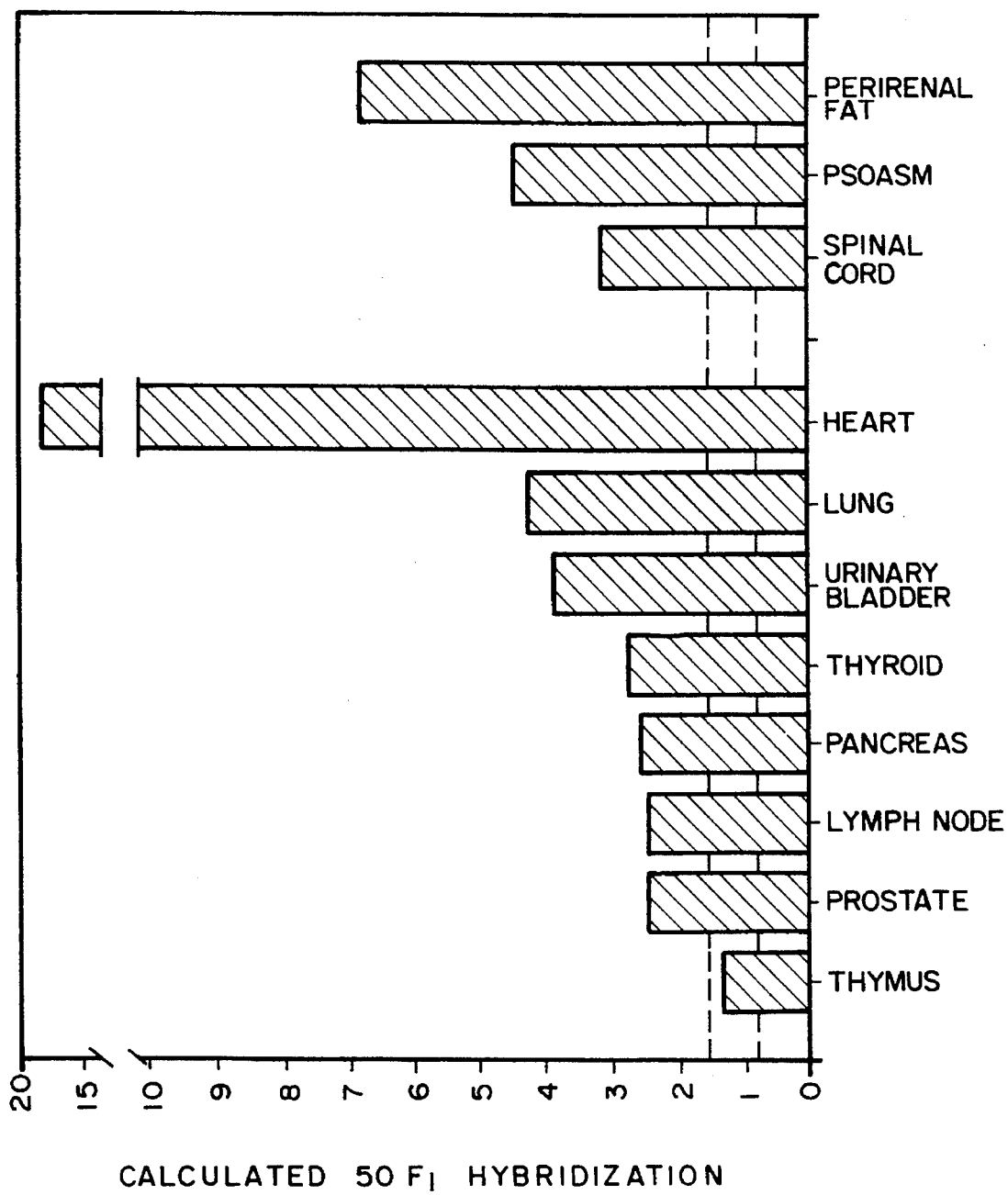
FIG. 6 is a bar diagram depicting copy number of 50F1 in different tissue samples.

The data in FIG. 6 extends this analysis to other adult tissues including: thymus, prostate, lymph node, pancreas, thyroid, bladder, lung, heart, spinal cord, psoasm muscle, and perirenal fat pad. A range of copy numbers of 50F1 is seen among these tissues.

Similar experiments utilizing either a v-Kirsten-ras probe or C-myc probe instead of 50F1 demonstrated that these sequences do not vary in copy number among human fetal and adult tissues.

The data of FIG. 1 illustrated the utility of evaluation of level of expression of sequence 50F1 for distinguishing between normally differentiated and benign and malignantly transformed colonic cells in vivo and in vitro. The data shown demonstrate that the copy number of 50F1 is elevated in normal colonic tissue, and varies among tissues and developmental stages, indicating that 50F1 is important in the processes of differentiation and transformation and clinically useful in characterizing the differentiation or transformation status of human colonic, and other, epithelial cells. Furthermore, the subject invention contemplates a method for determining the effectiveness of a material in regressing or inhibiting growth of colonic cancer comprising identifying a statistically significant differential in detected abundance of an RNA isolated from mammalian tissue or cells, said tissue having been subjected to contact with said material for a time sufficient to effect regression or inhibition of growth of colonic cancer, said differential being relative to a standard. Said standard being selected from a predetermined abundance obtained from normal or anormal populations.

The present invention also relates to polypeptides, or parts thereof, encoded by nucleic acid sequences, or parts thereof, wherein said nucleic acid sequences are characterized as possessing a copy number variably represented in different mammalian tissue. For example, the present invention is directed to the polypeptide or its derivatives (e.g., precursor) encoded by 50F1 and to the larger polypeptide encoded by the sequences adjacent to 50F1 in the genome.

The desired polypeptides are synthesized in vivo by first determining a nucleic acid sequence (RNA or DNA) encoding the amino acid sequencing comprising said polypeptide, inserting said nucleic acid sequence into an expression vector, transforming the resulting recombinant molecule into a suitable host and then culturing or growing the transformed host under conditions requisite for the synthesis of the polypeptide. The recombinant molecule defined herein should comprise a nucleic acid sequence encoding a desired polypeptide inserted downstream of a promoter, a eukaryotic or prokaryotic replicon and a selectable marker such as resistance to an antibiotic. The recombinant molecule may also require a signal sequence to facilitate transport of the synthesized polypeptide to the extracellular environment. Alternatively, the polypeptide may be retrieved by first lysing the host cell by a variety of techniques such as sonication, pressure disintegration or toluene treatment. Hosts contemplated in accordance with the present invention can be selected from the group comprising prokaryotes (e.g., *Escherichia coli*, Bacillus sp., Pseudomonas sp.) and eukaryotes (e.g., mammalian cells, yeast and fungal cultures, insect cells and plant cultures). The artisan will also recognize that a given amino acid sequence can undergo deletions, substitutions and additions of nucleotides or triplet nucleotides (codons). Such variations are all considered within the scope of the present invention. Techniques useful in practicing this aspect of the invention can be found in Maniatis et al., *Molecular Cloning: Laboratory Manual*, Cold Spring Harbor Laboratory, pages 1–500, 1982.

Alternatively, once the amino acid sequence is known, the polypeptide can be synthesized chemically (i.e., in vitro). In one example, a solid phase methodology of synthesis can be used starting with a resin to which the amino acid residue located at the amino end of the molecule is linked and to which subsequent amino acids, are selectively added. A resin commonly used in the art is benzhydrylamine (BHA resin) which is derived from a cross-linked polystyrene bead resin manufactured by copolymerization of styrene and divinylbenzene. Resin of this type is known and its preparation is further demonstrated by Pletta, et al., *Chem. Commun*, 650; 1970 and Orlowski, et al., *J. Org. Chem.* 41: 3701, 1976. In this synthesis, the amino acids are added one at a time to the insoluble resin until the total polypeptide sequence has been built up on the resin. The functional groups of the amino acids are protected by a blocking group. Blocking groups are well known in the art. For example, the alpha amino group of the amino acids can be protected by a tertiary butyloxycarbonyl group. The hydroxyl functions of serine and threonine can be protected by a benzyl or benzyl derivative group such as 4-methoxybenzyl, 4-methylbenzyl, 3,4-dimethylbenzyl, 4-chlorobenzyl, 2,6-dichlorobenzyl, 4-nitrobenzyl, benzhydryl or an equivalent thereof. The first amino acid residue (amino end) is coupled to the BHA resin by standard techniques such as under amide forming conditions. The blocked amino acid residue BHA produced above can then be deprotected by washing in a solvent with gentle agitation. Selected amino acids are then singularly added. At the end of the synthesis, the polypeptide is cleaved from the resin by, for example, treatment with hydrogen fluoride and then the polypeptide is purified using standard known techniques such as HPLC. The artisan will recognize variation in the aforementioned method as well as alternative synthesis techniques. All these are considered within the scope of the present invention.

The present invention also relates to antibodies to the aforementioned polypeptides. Such antibodies are contemplated to be useful in developing detection assays (immunoassays) for said polypeptides, especially during examination of biopsy tissue and in the purification of these polypeptides. The antibodies may be monoclonal or polyclonal. Additionally, it is within the scope of this invention to include any second antibodies (monoclonal or polyclonal) directed to the first antibodies discussed above. The present invention further contemplates use of these second antibodies in detection assays and, for example, in monitoring-the effect of an administered pharmaceutical preparation. Furthermore, it is within the scope of the present invention to include antibodies to the glycosylated regions of said polypeptides, and to any molecules complexed with said polypeptides. Accordingly, in accordance with this invention, an antibody to said polypeptides encompasses antibodies to the polypeptide, or part thereof, and to any associated molecules (e.g., glycosylated regions, lipid regions, carrier molecules, and the like).

The polypeptides, or parts thereof, considered herein are purified then utilized in antibody production. Both polyclonal and monoclonal antibodies are obtainable by immunization with the polypeptides, and either type is utilizable for immunoassays. The methods of obtaining both types of sera are well known in the art. Polyclonal sera are less preferred but are relatively easily prepared by injection of a suitable laboratory animal with an effective amount of the purified polypeptide, or part thereof, collecting serum from the animal, and isolating specific sera by any of the known immunoadsorbent techniques. Although antibodies produced by this method are utilizable in virtually any type of immunoassay, they are generally less favored because of the potential heterogeneity of the product.

The use of monoclonal antibodies in the present immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example, Douillard, J. Y. and Hoffman, T., "Basic Facts About Hybridomas", in *Compendium of Immunology*, Vol. II, L. Schwartz (Ed.) (1981); Kohler, G. and Milstein, C., *Nature* 256:495–497 (1975); *European Journal of Immunology*, Vol. 6, pp. 511–519 (1976), Koprowski, et al., U.S. Pat. No. 4,172,124, Koprowski et al., U.S. Pat. No. 4,196,265 and Wands, U.S. Pat. No. 4,271,145, the teachings of which are herein incorporated by reference.

Unlike preparation of polyclonal sera, the choice of animal is dependent on the availability of appropriate immortal lines capable of fusing with lymphocytes thereof. Mouse and rat have been the animals of choice in hybridoma technology and are preferably used. Humans can also be utilized as sources for sensitized lymphocytes if appropriate immortalized human (or nonhuman) cell lines are available. For the purpose of the present invention, the animal of choice may be injected with from about 1 mg to about 20 mg of the purified polypeptide, or part thereof. Usually the injecting material is emulsified in Freund's complete adjuvant. Boosting injections may also be required. The detection of antibody production can be carried out by testing the antisera with appropriately labeled antigen. Lymphocytes can be obtained by removing the spleen or lymph nodes of sensitized animals in a sterile fashion and carrying out fusion. Alternatively, lymphocytes can be stimulated or immunized in vitro, as described, for example, in C. Reading *J. Immunol Meth.*, 53: 261–291 1982.

A number of cell lines suitable for fusion have been developed, and the choice of any particular line for hybridization protocols is directed by any one of a number of criteria such as speed, uniformity of growth characteristics, deficiency of its metabolism for a component of the growth medium, and potential for good fusion frequency.

Intraspecies hybrids, particularly between like strains, work better than interspecies fusions. Several cell lines are available, including mutants selected for the loss of ability to secrete myeloma immunoglobulin. Included among these are the following mouse myeloma lines: $MPC_{11}$-X45- 6TG, P3-NS1-1Ag4-1. P3-X63-Ag8, or mutants thereof such as X63-Ag8.653, SP2-0-Ag14 (all BALB/C derived), Y3-'Agl.2.3 (rat), and U266 (human).

Cell fusion can be induced either by virus, such as Epstein-Barr or Sendai virus, or polyethylene glycol. Polyethylene glycol (PEG) is the most efficacious agent for the fusion of mammalian somatic cells. PEG itself may be toxic for cells, and various concentrations should be tested for effects on viability before attempting fusion. The molecular weight range of PEG may be varied from 1,000 to 6,000. It gives best results when diluted to from about 20% to about 70% (w/w) in saline or serum-free medium. Exposure to PEG at 37° C. for about 30 seconds is preferred in the present case, utilizing murine cells. Extremes of temperature (i.e., above 45° C.) are avoided, and preincubation of each component of the fusion system at 37° C. prior to fusion gives optimum results. The ratio between lymphocytes and malignant cells is optimized to avoid cell fusion among spleen cells and a range of from about 1:1 to about 1:10 gives good results.

The successfully fused cells can be separated from the myeloma line by any technique known by the art. The most common and preferred method is to choose a malignant line which is Hypoxanthine Guanine Phosphoribosyl Transferase (HGPRT) deficient, which will not grow in an aminopterin-containing medium used to allow only growth of hybrids and which is generally composed of hypoxanthine $1\times10^{-4}M$, aminopterin $1\times10^5M$, and thymidine $3\times10^{-5}M$, commonly known as the HAT medium. The fusion mixture can be grown in the HAT-containing culture medium immediately after the fusion 24 hours later. The feeding schedules usually entail maintenance in HAT medium for two weeks and then feeding with either regular culture medium or hypoxanthine, thymidine-containing medium.

The growing colonies are then tested for the presence of antibodies that recognize the antigenic preparation. Detection of hybridoma antibodies can be performed using an assay where the antigen is bound to a solid support and allowed to react to hybridoma supernatants containing putative antibodies. The presence of antibodies may be detected by "sandwich" techniques using a variety of indicators. Most of the common methods are sufficiently sensitive for use in the range of antibody concentrations secreted during hybrid growth.

Cloning of hybrids can be carried out after 21–23 days of cell growth in selected medium Cloning can be performed by cell limiting dilution in fluid phase or by directly selecting single cells growing in semi-solid agarose. For limiting dilution, cell suspensions are diluted serially to yield a statistical probability of having only one cell per well. For the agarose technique, hybrids are seeded in a semisolid upper layer, over a lower layer containing feeder cells. The colonies from the upper layer may be picked up and eventually transferred to wells.

Antibody-secreting hybrids can be grown in various tissue culture flasks, yielding supernatants with variable concentrations of antibodies. In order to obtain higher concentrations, hybrids may be transferred into animals to obtain inflammatory ascites. Antibody-containing ascites can be harvested 8–12 days after intraperitoneal injection. The ascites contain a higher concentration of antibodies but include both monoclonals and immunoglobulins from the inflammatory ascites. Antibody purification may then be achieved by, for example, affinity chromatography.

The presence of the polypeptides contemplated herein, or antibodies specific for same, in a patient's serum or biopsy tissue can be detected utilizing antibodies prepared as above, either monoclonal or polyclonal, in virtually any type of immunoassay. A wide range of immunoassay techniques are available as can bee seen byreference to U.S. Pat. Nos. 4,016,043, 4,424,279 and 4,018,653. This, of course, includes both single-site and two-site, or "sandwich" assays of the non-competitive types, as well as in traditional competitive binding assays. Sandwich assays are among the most useful and commonly used assays and are favored for use in the present invention. A number of variations of the sandwich assay technique exist, and all are intended to be encompassed by the present invention. Briefly, in a typical forward assay, an unlabeled antibody is immobilized in a solid substrate and the sample to be tested brought into contact with the bound molecule. After a suitable period of incubation, for a period of time sufficient to allow formation of an antibody-antigen binary complex, a second antibody, labeled with a reporter molecule capable of producing a detectable signal is then added and incubated, allowing time sufficient for the formation of a ternary complex of antibody-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labeled antibody are added simultaneously to the bound antibody, or a reverse assay in which the labeled antibody and sample to be tested are first combined, incubated and then added to the unlabeled surface bound antibody. These techniques are well known to those skilled in the art, and then possibly of minor variations will be readily apparent.

In the typical forward sandwich assay, a first antibody having specificity for the polypeptide, or part thereof, contemplated in this invention is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs or microplates, or any other surface suitable for conducting an immunoassay. The binding processes are well-known in the art and generally consist of cross-linking covalently binding or physically adsorbing the molecule to the insoluble carrier. Following binding, the polymer-antibody complex is washed in preparation for the test sample. An aliquot of the sample to be tested is then added to the solid phase complex and incubated at 25° C. for a period of time sufficient to allow binding of any subunit present in the antibody. The incubation period will vary but will generally be in the range of about 2–40 minutes. Following the incubation period, the antibody subunit solid phase is washed and dried and incubated with a second antibody specific for a portion of the hapten. The second antibody is linked to a reporter molecule which is used to indicate the binding of the second antibody to the hapten. By "reporter molecule," as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e., radioisotopes). In the case of an enzyme immunoassay, an enzyme is conjugated to the second antibody, generally be means of glutaraldehyde or periodate. As will be readily recognized, however, a wide variety of different conjugation techniques exist, which are readily available to the skilled artisan. Commonly used enzymes include horseradish peroxidase, glucose oxidase, B-galactosidase and alkaline phosphates, among other. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine, 5-aminosalicyclic acid, or tolidine are commonly used. It is also possible to employ fluorogenic substrates, which yield a fluorescent product rather than the chromogenic substrates noted above. In all cases, the enzyme-labeled antibody is added to the first antibody hapten complex, allowed to bind, and then the excess reagent is washed away. A solution containing the appropriate substrate is then added to the ternary complex of antibody-antigen-antibody. The substrate will react with the enzyme linked to the second antibody, usually visual signal, which may be further quantitated, usually spectrophotometrically, to give an indication of the amount of hapten which was present in the sample.

Alternately, fluorescent compounds, such as fluorescein and rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic color visually detectable with a light microscope. As in the EIA, the fluorescent labeled antibody is allowed to bind to the first antibody-hapten complex. After washing off the unbound reagent, the remaining ternary complex is then exposed to the light of the appropriate wavelength, the fluorescence observed indicates the presence of the hapten of interest. Immunofluorescence and EIA techniques are both very well established in the art and are particularly preferred for the present method. However, other reporter molecules, such as radioisotope, chemiluminescent or bioluminescent molecules, may also be employed. It will be readily apparent to the skilled technician how to vary the procedure to suit the required purpose. It will also be apparent that the foregoing can be used to detect directly or indirectly (i.e., via antibodies) the polypeptides of this invention.

Plasmid 50F1 is maintained in a culture of *Eschericichia coli* which has been deposited with the American Type Culture Collection 12301 Parklawn Drive, Rockville, Md. 20852 under the accession number ATCC67674.

The following examples further illustrate the present invention.

EXAMPLE 1

Preparation of RNA

Biopsy samples of human colonic mucosa, colonic adenomas and carcinomas are taken using a flexible colonscope and placed into liquid nitrogen within one minute of removal. The samples are stored in liquid $N_2$ until their use. RNA is prepared from the biopsy material by rapid disruption of the tissue in a buffer containing guanidinium isothiocyanate and pelleting the RNA through a cushion of CsCl as described by Maniatis, et al., Supra. PolyA+RNA is isolated by chromatography on oligo dT cellulose by the method of Aviv and Leder, supra. The PolyA+RNA is used to prepare $^{32}P$ labeled cDNA probes as described by Augenlicht and Kobrin, supra.

EXAMPLE 2

Scanning the Films and Data Digitization

Exposed x-ray film following hybridization of the library in a format is scanned with an Eikonix scanner, model 785, supported by a VAX 11/780 computer (Digital Equipment Corporation). The data are subsequently analyzed and processed using an IP 8500 image processing system (Gould) supported by the VAX 11/780 and an AP 120B x-ray processor (floating point system).

The Eikonix scanner records signal from the S-ray films in areas called pixels. The signal consists of the % transmitted light and is collected using a 45 mm wide angle lens. It is then converted to optical density for each pixel. The pixel size is set at 100×100 microns, and the film is therefore divided into a grid 2048×2048 pixels for a total of $4.19 \times 10^6$ individual measurements for each film (11 films=complete replica of the library hybridized to one probe). Each of these values represents an 8 bit optical density value obtained from a 12 bit transmission value.

The resultant image is first processed with a 5×5 median filter to suppress grain and other high frequency noise. This procedure replaces each pixel with the median value of the pixels in the 5×5 neighborhood surrounding it. Background is then subtracted in two steps. An intermediate image is produced from the median filtered image by choosing the minimum value of a 161 pixel horizontal line centered at the element being generated. The actual length of the line is not critical as long as it is wider than the region reserved for an individual clone. A second intermediate image is produced from the first in the same manner except that a maximum value is used in place of the minimum value. This image is then subtracted on a pixel by pixel basis to produce the processed image from which clone measurements are made.

EXAMPLE 3

Analysis of 50F1

The cDNA clone 50F1 was analyzed with respect to its nucleotide sequence and restriction cleavage pattern (restriction map).

A portion of the nucleotide sequence of the molecule cloned in the plasmid termed 50F1 is shown in FIG. 7 along with a partial restriction map of this portion of the plasmid. The sequence is shown as the reverse complement to present the open reading from position 45 to 227. Hence, the homopolymeric G sequence at the beginning of the sequence is located at the right end of the restriction map. This homopolymeric region was put on the end of the molecule by in vitro manipulation for cloning.

EXAMPLE 4

Hybridization Studies With 50F1

50F1, a 500bp cDNA clone, is useful as a probe for screening human genomic DNA for related sequences from adult and fetal tissue, including colon, placentas and HT29 cells and primary colon tumors. Using the methods contained herein, the 50F1 sequence is detected in high molecular weight DNA and, following digestion, in a single fragment whose size depends on the restriction enzyme used.

Rigorous quantitation of DNA dot blots indicates that, in contrast to human B β-globin, c-myc and c-ki-ras2 which remain constant, the copy number of 50F1 is elevated 6 fold in HT29 cells exposed to Na butyrate and an average of 3 fold in colon tumors relative to the DNA from several different placentas. A similar elevation is present in normal colon as early as 22 weeks of gestation. Further, the copy number varies amongst and is characteristic of different tissues and developmental stage. Thus, 50F1 is a sequence whose relative level of expression reflects the differentiation/transformation state of colon cells in vivo and in vitro and whose genomic copy number changes during development in the normal colon and other normal human tissues, suggesting an important role in normal differentiation.

What is claimed is:

1. A method for distinguishing between benign or malignantly transformed human colonic tissue and normal human colonic tissue by detecting a decrease in the abundance of RNA in a first sample of human colonic tissue which is to be studied compared to a second sample of human colonic tissue which is normal human colonic tissue wherein said RNA hybridizes to 50F1 complementary DNA standard probe, which method comprises:

(a) obtaining said first and second samples of human colonic tissue and RNA thereof;
    (b) immobilizing said RNA of said first and second samples separately and contacting said RNA in said first and second samples under hybridization conditions with said 50F1 complementary DNA standard probe consisting of the sequence set forth in FIG. 7 to form first and second hybridized RNA/DNA complexes, respectively;
    (c) measuring the quantity of said first and second hybridized RNA/DNA complexes; and
    (d) comparing said quantity of hybridized complex formed between the RNA in said first sample and said 50F1 complementary standard DNA probe with the quantity of hybridized complex formed between the RNA in said second sample and said 50F1 complementary DNA standard probe, wherein detecting a decrease in abundance of RNA in said first sample relative to the amount of RNA in said second sample distinguishes between human colonic tissue which is benign or malignantly transformed and normal human colonic tissue.

2. A method for monitoring the state of premalignant or malignant human colonic tissue by measuring a change in the abundance of RNA in a first sample of human colonic tissue which is to be studied compared to a second sample of human colonic tissue, wherein said second sample is a predetermined sample from malignant or benignly transformed human colonic tissue, and wherein said RNA hybridizes to a 50F1 complementary DNA standard probe which method comprises:

(a) obtaining said first and second samples of human colonic tissue and RNA thereof;
    (b) immobilizing said RNA of said first and second samples separately and contacting said RNA in said first and second samples under hybridization conditions with said 50F1 complementary DNA standard probe consisting of the sequence set forth in FIG. 7 to form first and second hybridized RNA/DNA complexes, respectively;
    (c) measuring the quantity of said first and second hybridized RNA/DNA complexes and
    (d) comparing said quantity of hybridized RNA/DNA complex formed between the RNA in said first sample and said 50 F1 complementary standard DNA probe with the quantity of hybridized RNA/DNA complex formed between the RNA in said second sample and said 50F1 complementary DNA standard probe, wherein a change in the abundance of RNA in said first sample relative to that in said second sample signifies a change in the state of the premalignant or malignant human colonic tissue.

3. The method according to claim 1 or 2 wherein the RNAs of said first and second samples independently comprise total cellular RNA.

4. The method according to claim 1 or 2 herein the RNAs of said first and second samples independently comprise poly (A) RNA.

5. The method according to claim 1 or 2 wherein said first and second samples of human colonic tissue are obtained from human colonic mucosa.

6. The method according to claim 1 or 2 wherein said 50F1 complementary DNA standard probe is labeled with a radioactive isotope.

7. The method according to claim 6 wherein comparing said quantity in step (d) comprises comparing the counts per minute of radioactivity in said first hybridized complex with the counts per minute of radioactivity in said second hybridized complex.

8. The method according to claim 7 wherein step (d) comprises:

(i) exposing said first hybridized complex to x-ray film and said second hybridized complex to x-ray film;
    (ii) reading the x-ray films of said first and second hybridized complexes with an optical scanner to produce a signal for each complex;
    (iii) converting each signal to digital data; and
    (iv) comparing said digital data from the hybridized complexes.

9. The method according to claim 1 or 2 wherein said 50F1 complementary DNA is maintained in a culture of *Escherichia coli*, having ATCC accessing number 67674.

\* \* \* \* \*

UNITED STATES PATENT AND TRADEMARK OFFICE
CERTIFICATE OF CORRECTION

PATENT NO. : 5,569,584
DATED : October 29, 1996
INVENTOR(S) : Leonard H. Augenlicht It is certified that error appears in the above-indentified patent and that said Letters Patent is hereby corrected as shown below:

Column 5, line 47: "eachsample" should read --each sample--

Column 9, lines 48-49: "1X10⁻4M" should read --$1X10^{-4}M$--

Column 10, line 24: "byreference" should read --by reference--

Column 12, line 37: "films=complete" should read --films=1 complete--

Column 13, line 17: delete "$\beta$"

Column 14, line 23, Claim 2: "50 Fl" should read --50Fl--

UNITED STATES PATENT AND TRADEMARK OFFICE
CERTIFICATE OF CORRECTION

PATENT NO. : 5,569,584
DATED : October 29, 1996
INVENTOR(S) : Leonard H. Augenlicht It is certified that error appears in the above-indentified patent and that said Letters Patent is hereby corrected as shown below:

Column 14, line 34, Claim 4: "herein" should read --wherein--

Column 14, line 36, Claim 4: "(A) RNA" should read --$(A)^+$ RNA--

Column 14, line 61, Claim 9: "accessing" should read --accession--

Signed and Sealed this

Sixth Day of May, 1997

Attest:

BRUCE LEHMAN

Attesting Officer

Commissioner of Patents and Trademarks